United States Patent [19]

Quate et al.

[11] Patent Number: 4,567,767
[45] Date of Patent: Feb. 4, 1986

[54] METHOD AND APPARATUS FOR VERY LOW TEMPERATURE ACOUSTIC MICROSCOPY

[75] Inventors: Clavin F. Quate; John Foster, both of Stanford; Daniel Rugar, Palo Alto, all of Calif.

[73] Assignee: The Board of Trustees of the Leland Stanford Junior University, Stanford, Calif.

[21] Appl. No.: 610,352

[22] Filed: May 14, 1984

[51] Int. Cl.[4] ............................................. G01N 29/04
[52] U.S. Cl. ....................................................... 73/606
[58] Field of Search .................. 73/606, 607, 644, 642; 310/335, 336

[56] References Cited
U.S. PATENT DOCUMENTS
4,378,699 4/1983 Wickramasinghe .................. 73/644

OTHER PUBLICATIONS

D. Rugar et al., "Acoustic Microscopy at Temperatures Less than 0.2° K.", *Acoustic Imaging*, vol. 12, pp. 13–25, 1982.

Primary Examiner—Stephen A. Kreitman
Attorney, Agent, or Firm—Flehr, Hohbach, Test Albritton & Herbert

[57] ABSTRACT

A method and apparatus for imaging objects utilizing acoustic waves at frequencies above 4.2 Ghz and up to 8 Ghz wherein the transducer and the object imaged by waves or beams from the transducer are both at a temperature no greater 0.2° K. The transducer is driven by pulses generated by a short pulse generator which are stretched and coded by a dispersive filter and inductively coupled to a low temperature coupler to be use to drive the transducer. The frequency returns are carried by the same bidirectional coupler to a low noise amplifier. Both the low noise amplifier and bidirectional coupler are maintained at a temperature of less than 4.2° K. The output of the amplifier is then coupled to a dispersive filter which responds the coding in the first dispersive filter to decode the information and reconstruct the signal. Subsurface defects are detected by heating the object while it is inspected by the acoustic transducer.

19 Claims, 3 Drawing Figures

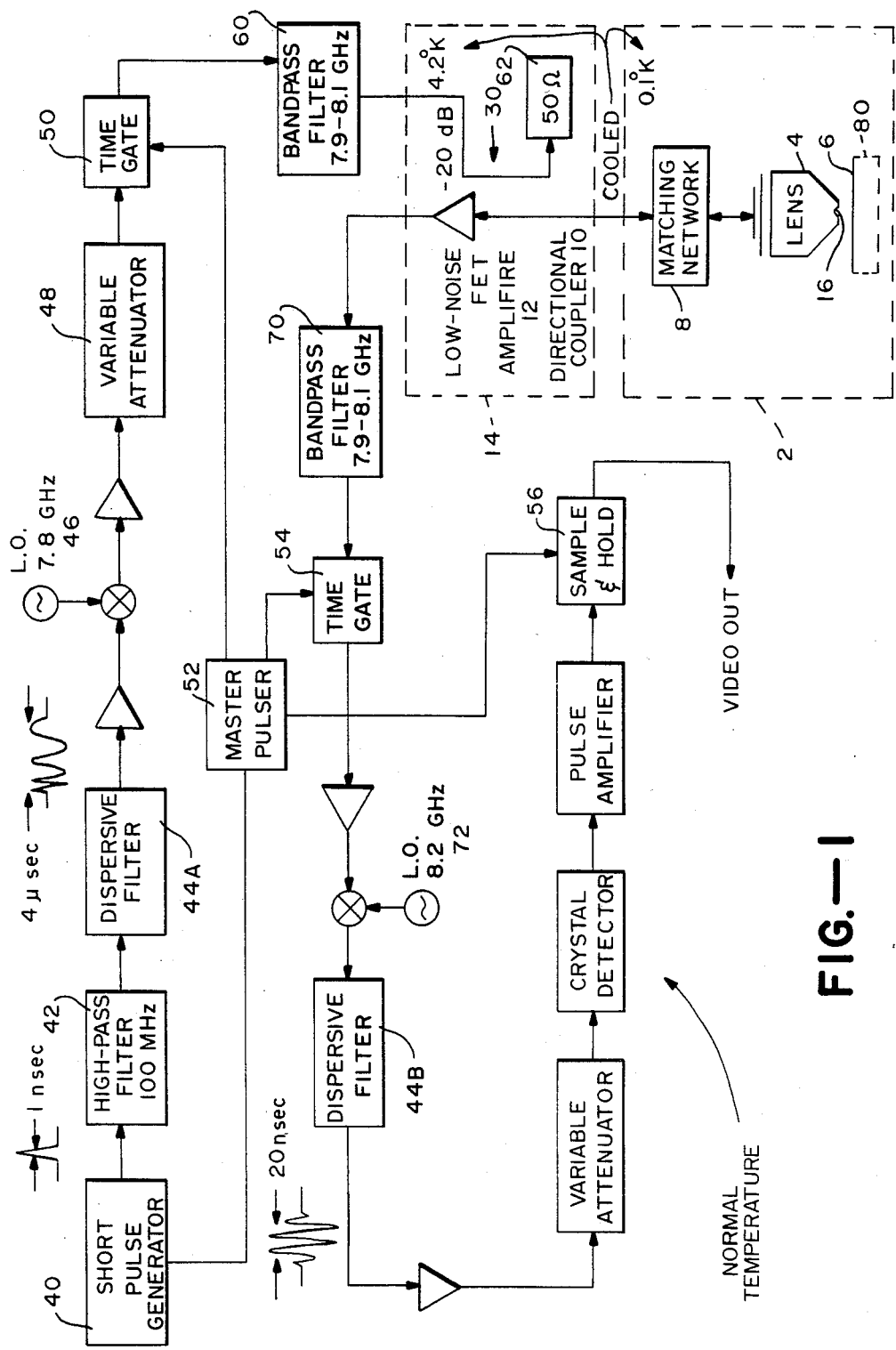
FIG.—1

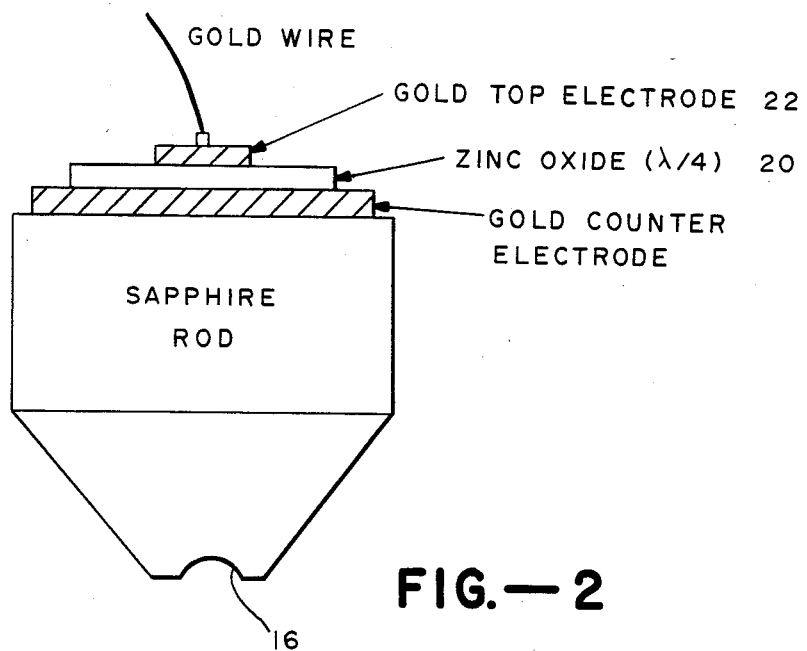
FIG.—2
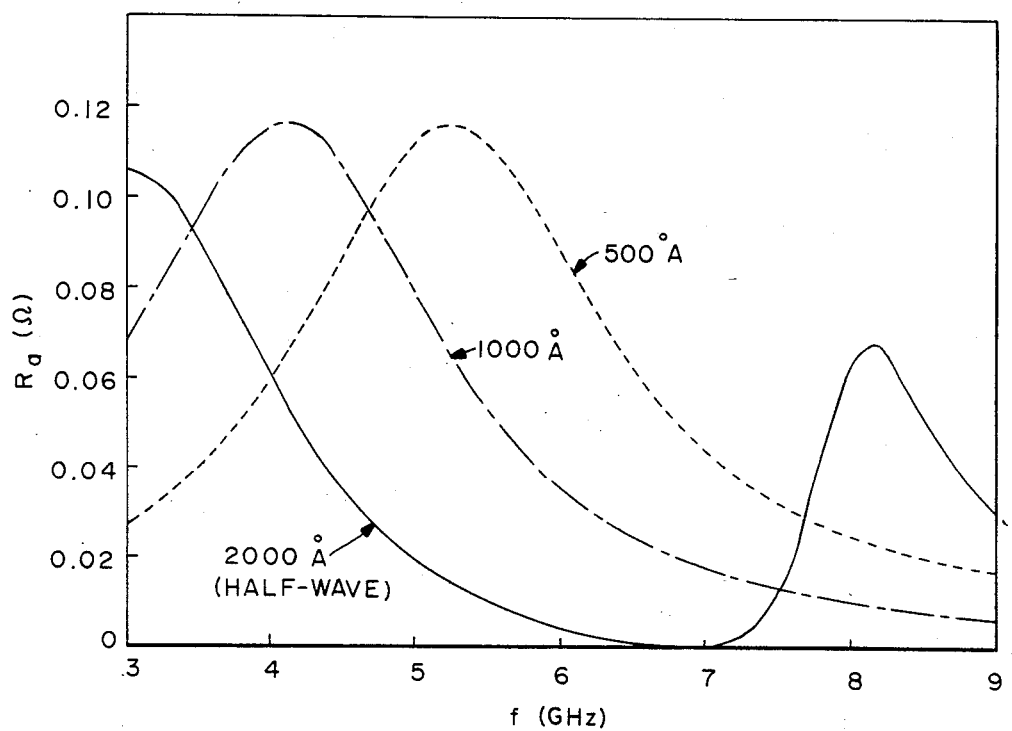
FIG.—3

METHOD AND APPARATUS FOR VERY LOW TEMPERATURE ACOUSTIC MICROSCOPY

The U.S. Government has rights in this invention described and claimed herein pursuant to Contract No. N00014-77-C-0412.

This invention is directed generally to the field of acoustic microscopy and more particularly to a method and apparatus for imaging of objects utilizing acoustic waves wherein the transducer, the sample, and the pulse coupling apparatus are cooled to very low temperatures.

Acoustic microscopes have become quite well known as a means of very high resolution microscopy since their disclosure in the Feb. 15, 1974 of Applied Physics Letters in an article entitled: "Acoustic Microscope, Scanning Version" at pages 163ff and authored by Lemons and Quate, or as further disclosed in U.S. Pat. No. 4,012,950 to Kompfner, Chodorow, and Lemons both incorporated by reference. Generally speaking, acoustic imaging involves as a first step the generation of one or more radio frequency signals typically in the microwave frequency region. The signals are delivered to an electric transducer which generates bulk acoustic waves of short wave length in the form of a collimated beam in an acoustic propogating medium. Each acoustic beam is then delivered to an acoustic lens which effects a sharp convergence of the beam to a focal point where the object to be imaged is positioned. A non-linear action of the impinging acoustic energy occurs either within the object itself or in the adjacent medium so as to generate frequencies which are different from those applied or to change the amplitude of the applied frequency. This reflected output acoustic energy is subsequently detected, converted into an electric signal, and delivered to an oscilloscope or other mechanism for displaying the optical image of the object can be displayed. However, the resolution of the acoustic microscope is presently limited by the sound wavelength and the coupling fluid between the lens and the sample.

It is therefore an object of the present invention to provide an improved acoustic microscope capable of operating at much higher frequencies and thus shorter wave lengths then previously used.

It has been found that the use of cryogenic fluids as a medium to cool the transducer and object offers two advantages over room temperature fluids for use in acoustic microscopy: low sound speed, and low acoustic attenuation. Liquid Nitrogen, Argon, and Helium have all been used. However, liquid helium emerges as the ultimate fluid for high resolution acoustic microscopy because of its near zero acoustic attenuation at very low temperatures.

It is an objective of the present invention to optimize the frequency capability of an acoustic microscope using cryogenic fluids to cool the lens and sample.

In a book entitled ACOUSTIC IMAGING, volume 12, edited by Eric A. Ash and C. R. Hill and published by Planham publishing Corporation in 1982 article by D. Rugar, J. S. Foster, and J, Heiserman entitled ACOUSTIC MICROSCOPY AT TEMPERATURES LESS THAN 0.2° K., incorporated herein by reference, a disclosure is made of an acoustic microscope scanner and appropriate cryogenic fluids to achieve an microscope operating frequency of up to 2.6 GHz. However, as the frequency of the microscope is increased to these gigahertz levels, a fundamental problem intervenes of limiting the signal to noise ratio of the instrument.

It is an objective of the present invention to achieve operating frequencies of a helium acoustic microscope of at least 4.2 GHz and it is a further objective to extend the operating frequency of the microscope to 8 GHz, thereby obtaining a lateral resolution of 200 A with acceptable signal to noise ratio levels.

BRIEF SUMMARY OF THE INVENTION

The signal to noise problem in the present invention is reduced by an adaptation of a low noise amplifier previously disclosed by S. Weinreb IEEE Transactions Microwave Theory Tech. 28, 1041 (1980) in which an FET amplifier for use in astronomy is disclosed operating at temperatures as low as 20° k. In the present invention, the operating temperature of this amplifier is reduced even lower, and the amplifier is coupled to the output circuit from the acoustic transducer of the acoustic microscope. To further enhance the signal to noise ratio and maintain the input power of the system a know pulse compression technique is used to generate a high frequency pulse train which is impressed on the basic operating frequency (at least 4.2 GHz, up to 8 GHz) by using room temperature components. This pulse train is passed on a wire close to a super cooled transmission line which serves a directional coupler between the low noise amplifier and the transducer. By use of this super cooled transmission line, extremely low losses in the input pulse frequency which drives the transducer are achieved; further, the output frequency from the transducer to the amplifier are coupled over this same super cooled transmission line to minimize losses and optimize the signal to noise ratio.

In a further improvement over known low temperature acoustic microscopes, a transducer has been designed to give maximum conversion efficiency between the electric and acoustic powers with reasonably uniform distribution of the acoustic field over the lens aperture and minimum amount of power loss due to sound waves falling outside the lens.

In known acoustic transducers, the radius of the transducer is usually two to three times the radius of the lens aperture. In the transducer according to the present invention, the radius of the transducer is approximately the same size as the aperture, or about 125 micrometers. Surprisingly, it has been discovered that this size of transducer is the most efficient in receiving the field from the lens aperture at these extremely high frequencies. The field is generated using a top electrode on the top surface of the transducer. It has been found that the thickness of this top layer electrode is also critical to the efficiency of the system again, surprisingly, it has been found that a 2000 A (half wave) thick electrode provides the optimum conversion efficiency at frequencies of at least 4 GHz and as high as 8 GHz.

Yet another limitation on known low temperature acoustic microscopes, is that effective imaging only occurs on the top surface of the specimen. It is therefore an object of the present invention to provide a means for effectively imaging below the surface of the object.

This objective is achieved by heating the cryogenically cooled object while imaging is occurring. In the preferred embodiment, heating is applied to a surface of the object which is opposite to the surface being imaged. Alternatively, the object may be self heated by turning on an integrated circuit. In either case, the radiated heat turns to sound waves when it passes out of the object into the cryogenic fluid to effectively modulate the incoming acoustic wave; since at these temperatures any voids below the surface function effectively are a vacuum, the heat or sound waves are effectively modified by the presence of such voids and thus become apparent on analysis of the reflected radiation. The heat or sound waves are also effectively modified by material defects and changes below the surface.

The above objective of the invention and the manner in which they are achieved will be more readily understood by reference to the following detailed description with reference to a specific embodiment of the invention shown in the accompanying drawings wherein:

BRIEF DESCRIPTION OF THE DRAWINGS

FIG. 1 is a schematic showing both the room temperature circuitry and the super cooled circuitry and transducer and sample which make up the acoustic microscope of the present invention;

FIG. 2 is a cross-sectional view of a transducer which is especially useful with the present invention; and FIG. 3 is a graph showing the variation of transducer radiation resistance as a function of frequency for different top electrode thickness which may be utilized to optimize selection of a transducer.

DETAILED DESCRIPTION

The mechanically scanned acoustic microscope 2 shown in FIG. 1 utilizes a fluid cryogenic medium to couple sound from the acoustic lens 4 to a reflecting sample 6. The sound waves from the acoustic lens are generated using the room temperature electronics shown in general in FIG. 1. The signals generated which preferably are at least over 4 Ghz and preferably 8 Ghz, are coupled through a matching network 8 to the lens through a super conducting directional coupler 10. The coupler 10 together with the low noise amplifier 12 for amplifying the output signals are cooled to extremely low temperatures. In this manner, by cooling the lens and sample to less than 0.2° K. and preferably to 0.1° K., and by cooling the amplifier and directional coupler to no more than about 4.2° k., the microscope can effectively operate in the reflection mode at above 4.2 GHz and has a demonstrative effectiveness at a preferred frequency of 8 GHz.

In a preferred embodiment, the microscope is cooled by an HE3-HE4 dilution refrigerator. The acoustic lens 4 is mounted on a mechanical positioner which translates the lens in a raster pattern to form the image as disclosed in detail in the incorporated portion of the book ACOUSTICAL IMAGING.

The lens itself is of a special design to give maximum conversion efficiency between electrical and acoustic powers with a reasonably uniform distribution of the acoustic field over the lens aperture 16 with a minimum amount of power loss due to sound waves falling outside the lens. The transducer used in the present invention is especially useful at frequencies in the realm of 8 GHz. In known transducers for acoustic imaging, the transducer radius is usually two to three times the radius of the lens aperture as a trade off between these factors. The radius of the transducer 20 here is chosen to be approximately the same size as the aperture 16 or about 125 micrometers. Thus the acoustic field distribution on the lens surface due to these transducers is not relatively uniform; but a larger size transducer which would give a more uniform illumination cannot be used because it becomes quite inefficient as the size is increased.

At frequencies around 8 GHz, the two critical transducer parameters which determine the conversion efficiency and band width are the thickness of the gold top electrode 22, and the radius of the transducer 20. A cross section of typical transducer is shown in FIG. 2; the variation of transducer radiation resistance as a function of frequency for different top electrode thicknesses is shown in FIG. 3. FIG. 3 thus clearly demonstrates the effectiveness for an 8 Gigahertz system of a 2000 angstrom thick electrode. In a design of the transducer it has to be taken into account that the top electrode 22 effectively loads the transducer and changes the resonant frequency. To minimize the effect of the loading, one would like the electrode thickness to be either very thin with respect to an acoustic wave length or some multiple of the half wave length. Gold has a sound velocity of 3.21 Km/s and hence the 500 to 1000 A thick top electrodes usually used in low frequency application would be $\frac{1}{8}$ to $\frac{1}{4}$ wave thick at 8 GHz. Making the top electrode significantly thinner than 500 A becomes impractical because of the increased resistive loss with a thinner film. FIG. 3 thus demonstrates that a 2000 A (half wave) thick electrode should be used to get the optimum conversion efficiency at 8 GHz even though the acoustic band width is small due to the acoustic resonance in the top electrode.

It has also been calculated that 125 micrometer or larger transducers give very small radiation resistance and reactance as compared to larger ones. The finally consideration in the design is that the transducer must be large enough to illuminate the lens aperture 16 but not be to large which results in reduced efficiency. It was through these considerations that the design of the transducer especially useful at higher frequencies than 4 GHz and specifically at 8 GHz was evolved.

Also crucial to the noise performance of the microscope is the system 14 which amplifies and detects the microwave signals from the acoustic transducer. A superconducting coaxial transmission line 10 which also functions as a directional coupler connects the transducer 4 to a two stage low noise gallium arsenide field effect transistor pre amplifier which is located in the same 4.2 K. helium bath of the refrigerator. By locating this coaxial transmission line in the same 4.2° K. environment, an extremely low loss coupler is achieved which is capable of transferring the detected signal from the lens to the amplifier 12.

The receiving system band width, determined by a room temperature intermediate frequency amplifier shown in the remainder of FIG. 1 and to be described below is 20 Mhz. The transmitted RF pulses are generated by room temperature components, and are coupled into the coaxial line leading to the transducer by a directional coupler 30 also located within the low temperature environment. Specifically, a 20 Mhz generator combined with a local oscillator having a 7.8 GHz output provides an 8 GHz signal runs through a wire which is placed closely adjacent the low loss transmission line 10. In this manner, the microwave signals for driving the lens are inductively coupled into the transmission line. By using such coupling, room temperature thermal noise from the transmitting system does not degrade the noise performance of the receiving system.

Turning now to the room temperature electronics of FIG. 1, these generate and receive the RF level signal which effectively determines the system band width. Specifically, a short pulse generator 40 generates a relatively short pulse as shown of about 1 nanosecond duration. This is filtered in filter 42 and passed to the dispersive filter 44. The dispersive filter which is of a type already known in the art, takes the short pulse and turns it into a longer duration pulse which is effectively frequency coded as a function of time. It should be noted that the two dispersive filters 44A in the frequency generator and 44B in the frequency receiver, are effectively mirror images of each other in the sense that the dispersive filter in the frequency receiver portion will recognize the coding applied by the dispersive filter in the transmitting section. The 200 megahertz signal is mixed with a local oscillator output 46, to provide the desired 8 GHz transmission frequency. This signal is then again amplified and attenuated as necessary at 48. The duration of the 8 GHz signal to be used to drive the acoustic transducer is defined by the time gate 50 so that for example if the transducer is to be driven for a period of 4 microseconds, then a space of 4 microseconds for the receipt of the reflections is provided by the master pulse driver 52. This pulse driver also drives the original short pulse generator, and a time gate in the signal output lines 54 as well as a sample and hold device 56 for capturing the information content of the reflected signals from the transducer. The 8 GHz signal is then passed through a band pass filter 60 to screen out any signals which are not at or very close to the desired 8 GHz frequency. The output of the band pass filter is then coupled as previously described in the super cooled section to the low loss directional coupler 10 to be transferred to the matching network and the transducer. The 50 ohm resistor is provided as a termination on the wire carrying the 8 GHz signal to match it with the resistance in the line coupling it to the transducer, as well as to prevent unnecessary reflections of the 8 GHz signal.

The 8 GHz signal is now transferred to the lens which is excited and launches the plane waves to the substrate 6; reflections are received at the lens and pass through the superconducting coaxial line 10 to the super cooled low noise amplifier. Because the superconducting coaxial transmission line functions to carry the signals to the transducer and the reflected signals which contain the actual information content about the surface of the object 6 back to the low noise amplifier, its design is critical to the effective performance of this system.

The reflections from the sample are passed through band pass filter 70, through timing gate 54 and mixed at local oscillator 72 to provide a difference signal which is once again 200 MHZ. The dispersive filter can now effectively decode the long pulse and convert it back to a short pulse shown as of about 20 nanoseconds, which effectively contains the information content of the signal. The use of this coding technique allows the system to use a pulse of small amplitude and long duration in the transmitting system and convert it to a high amplitude short duration pulse in the receiving system; this is important since the system is limited on the input power which can be used to drive the transducer.

The output of the dispersive filter is attenuated as desired, amplified and stored for display on a video display to build up a complete picture of the surface of the sample as the microscope is scanned across the surface.

The use of the bidirectional coupler is a significant change from the three port circulator most commonly used in such applications. In such a device, the input is applied to one of three possible ports, and circulates to the next port where it is transmitted out to drive the transducer; the return reflections are received at the same circulator port and again circulate in the same direction as the input pulses to the next or third port where they are applied to appropriate decoding circuitry. Such circulators do not work effectively at extremely low temperatures such as must necessarily be used on the input to the low noise super cooled amplifier.

In a further advantageous modification of the present invention, it has been found that by heating the sample under inspection, information under the surface can be detected, even in this cryogenic atmosphere. It is known that in such cryogenic detection systems, the reflections all occur directly from the surface of the object i.e. there is little or no sub-surface penetration nor is it possible to focus the lens at a point below the surface to inspect under the surface. All experiments to date have demonstrated that reflections off the sample surface 6 is effectively perfect in this cryogenic situation. It has been found that by putting a heater 80 on the back side of the object under examination, that in fact the sound waves pass through the device and emerge from the surface as sound waves which modulate the incoming acoustic waves. The same effect occurs if the device itself is heated, as for example by turning on a integrated circuit. Heat waves at these temperatures are just incoherent sound, as opposed to the coherent sound waves which emerge from the aperture 16 of the transducer. Thus as the sound waves travel through the crystal, if they come to a defect as for example a hole or divot or defect in the device, their path of travel is blocked, since at these temperatures, such an opening or defect will scatter the incoherent sound waves. Thus while sound waves coming toward the aperture will be detected in all solid areas of the sample, if internal holes exist, for example, travel of the sound waves will be blocked and no sound waves will emerge from the top surface of the device under examination. Since the incoming sound waves from the heat source and the coherent waves from the transducer meet above the surface 6 under inspection, they effectively scatter off each other, reducing the strength of the signal which will be reflected back and detected in the acoustic microscope system. The net effect is a scattering of the acoustic phonons which make up the coherent planar sound waves transmitted by the transducer 4; they are scattered by the heater phonons which emerge from the surface 6 under inspection. The fact that the heater waves will emerge from the surface is a result of what is known as the KAPITZA anomaly. The anomaly states that high frequency sound does pass through the surfaces, and it has been determined that such high frequency sound is easily developed with a heater 80.

Other modifications or alternative embodiments of the present invention may become apparent to one of skill in the art who has reviewed the above disclosure. Therefore, the scope of the present invention is not to be limited to the preferred embodiment which is described above, but only by the claims which follow.

What is claimed is:

1. A method of acoustic imaging a sample utilizing an acoustic beam at an imaging frequency greater than 4 GHz comprising generating a high frequency pulse train, cooling said object to a very low temperature, coupling said pulses to a transducer for imaging said object through a directional coupler in a very low temperature atmosphere, detecting the acoustic energy reflected from said object through said bidirectional coupler to an amplifier in said low temperature atmosphere, and converting said detected energy to an electrical output signal.

2. A method as claimed in claim 1 wherein said directional coupler is cooled to a temperature no greater than 4.2° k.

3. A method as claimed in claim 1 wherein said bidirectional coupler and said amplifier are cooled to a temperature no more than about 4.2° k.

4. A method as claimed in claim 3 wherein the high frequency pulses are generated by components maintained at room temperature.

5. A method as claimed in claim 4 wherein said bidirectional coupler comprises a superconducting transmission line.

6. A method as claimed in claim 5 wherein said pulse stream is coupled by induction to said transmission line within the cooled region.

7. A method as claimed in claim 6 wherein said object is heated during said imaging step.

8. A method as claimed in claim 7 wherein said heat is applied to said object on the side opposite the impingement of said acoustic waves.

9. Acoustic imaging apparatus comprising an acoustic transducer for imaging an object with high frequency acoustic energy,
means for driving said acoustic transducer at a frequency of at least 4 Ghz,
means for cooling said acoustic transducer and said object to less than 0.2° k.,
means for receiving the reflected acoustic energy from said object including an amplifier and a directional coupler between said transducer and said amplifier,
means for cooling said amplifier and coupler.

10. Apparatus as claimed in claim 9 wherein said driving means includes a short pulse generator and dispersive filter for coding said input frequency, and said receiving means includes a dispersive filter and detector for decoding said reflected acoustic energy.

11. Apparatus as claimed in claim 9 wherein said directional coupler cooled to a temperature no greater than 4.2° k.

12. Apparatus as claimed in claim 9 wherein said directional coupler and amplifier are cooled to a temperature no greater than 4.2° k.

13. Apparatus as claimed in claim 12 wherein said dispersive filters and pulse generator and detector are maintained at about room temperature.

14. Apparatus as claimed in claim 11 wherein said directional coupler is a bidirectional coupler including a superconducting transmission line.

15. Apparatus as claimed in claim 14 wherein said driving means includes means for inductively coupling said acoustic transducer driving frequencies to said transmission line.

16. Apparatus as claimed in claim 15 including means for heating said cooled object during acoustic imaging.

17. Apparatus as claimed in claim 16 wherein said heating means heat a surface of said object opposite to said acoustically imaged surface of the object.

18. Apparatus as claimed in claim 17 wherein said transducer has a driving electrode of about 2000 Å thickness.

19. Apparatus as claimed in claim 18 wherein said transducer has a radiating aperture of radius about 125 mm.

* * * * *

UNITED STATES PATENT AND TRADEMARK OFFICE
CERTIFICATE OF CORRECTION

PATENT NO. : 4,567,767
DATED : February 4, 1986
INVENTOR(S) : Quate et al.

It is certified that error appears in the above-indentified patent and that said Letters Patent is hereby corrected as shown below:

Column 1, line 3

--This invention was made with Government support under contract N00014-77-C-0412 awarded by the Department of the Navy. The Government has certain rights in this invention.--

Signed and Sealed this

Fourth Day of April, 1995

Attest:

BRUCE LEHMAN

*Attesting Officer*  *Commissioner of Patents and Trademarks*